United States Patent [19]

Grass et al.

[11] Patent Number: 4,489,426
[45] Date of Patent: Dec. 18, 1984

[54] COLLIMATOR WITH ADJUSTABLE APERTURE

[75] Inventors: Joseph J. Grass; Robert J. Dobberstein, both of Brookfield, Wis.

[73] Assignee: General Electric Company, Schenectady, N.Y.

[21] Appl. No.: 334,032

[22] Filed: Dec. 23, 1981

[51] Int. Cl.³ .................................... G03B 41/16
[52] U.S. Cl. ................................ 378/150; 378/147
[58] Field of Search .......................... 378/150, 147

[56] References Cited

U.S. PATENT DOCUMENTS

| | | | |
|---|---|---|---|
| 794,788 | 7/1905 | Custer | 378/ |
| 2,412,662 | 12/1946 | Watson | 378/147 |
| 2,546,699 | 3/1951 | Poittevin | 378/ |
| 2,558,492 | 6/1951 | Lely | 378/ |
| 2,659,017 | 11/1953 | Bartow | 378/ |
| 3,569,712 | 3/1971 | Avakoff | 378/ |
| 3,588,511 | 6/1971 | Montagne | 378/ |
| 3,631,249 | 12/1971 | Friede | 378/ |
| 3,849,649 | 11/1974 | Carey | 378/ |
| 3,912,936 | 10/1975 | Cunningham | 378/ |
| 3,944,836 | 3/1976 | Peret | 378/ |
| 3,947,689 | 3/1976 | Wagner | 378/ |
| 4,048,498 | 9/1977 | Gerlach | 378/ |
| 4,118,632 | 10/1978 | Luig | 378/150 |

Primary Examiner—Craig E. Church
Attorney, Agent, or Firm—Fuller, House & Hohenfeldt

[57] ABSTRACT

Collimator for regulating the shape and size of the pattern of radiation projected on a radiation detector from a radiation source, particularly for regulating the beam of radiation in a medical diagnostic x-ray machine. One or more (preferably three) longitudinally stacked plates are provided, the top plate having a large aperture, the middle plate having a medium sized aperture, and the lower plate having a small aperture. The middle and lower plates are provided with means to substantially open up their apertures, rendering these plates inactive when they are not in use. Each plate is longitudinally movable between first and second extremities of travel, the first extremity being nearest the radiation source. When each plate is at its first extremity of travel the beam of radiation has its maximum size. The size is first reduced by advancing the first plate longitudinally to its second extremity of travel, then by placing the second in its active position in the beam and advancing it to its second extremity of travel, and finally by placing the third plate in its active position in the beam and advancing the third plate to its second extremity of travel. A drive means and associated structure is also disclosed for placing the plates in their active positions and advancing the three plates. The present invention allows continuous variation of the size of the x-ray beam projected on the detector over a wide range, while at the same time providing a collimator which is longitudinally compact. The collimator can be provided with apertures of any shape, allowing projection of an irregularly shaped pattern which is continuously variable in size.

9 Claims, 13 Drawing Figures

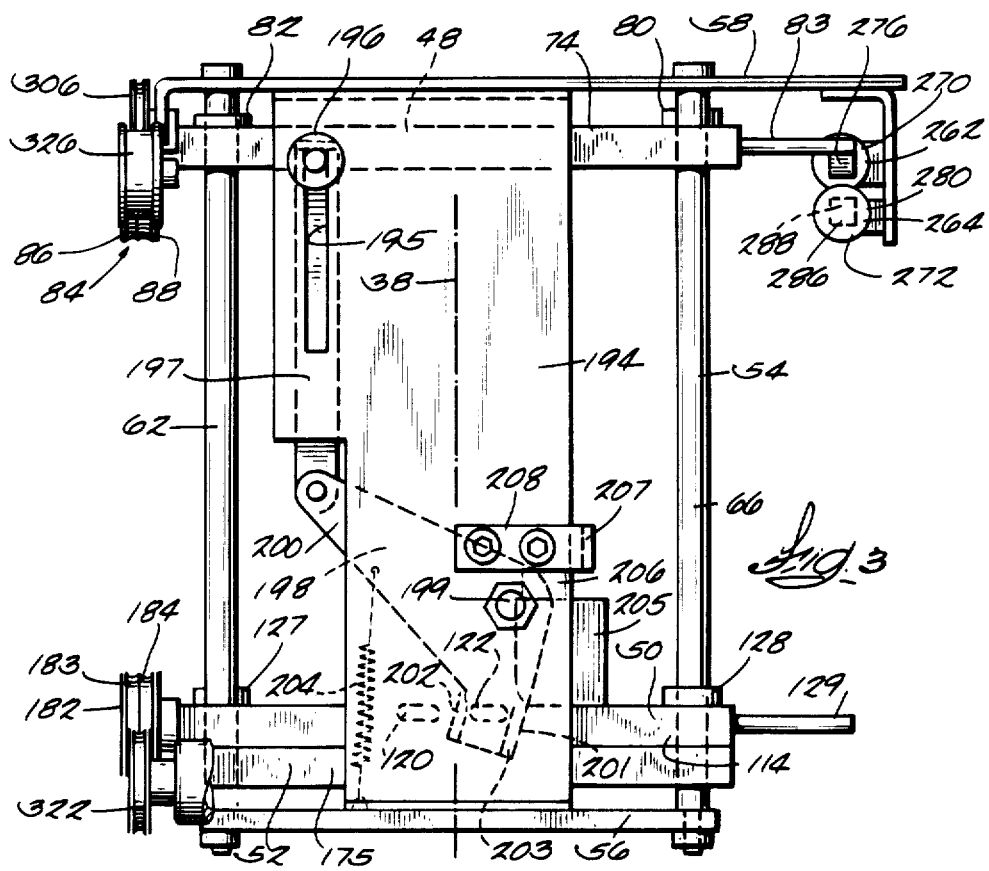
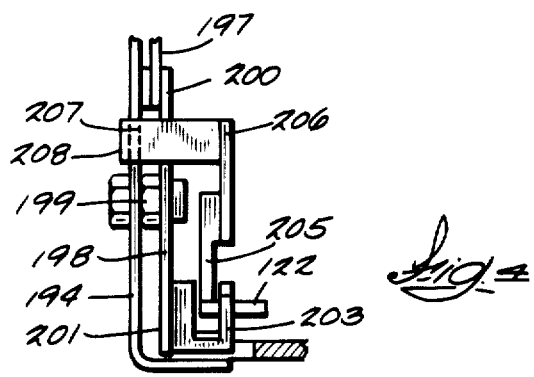

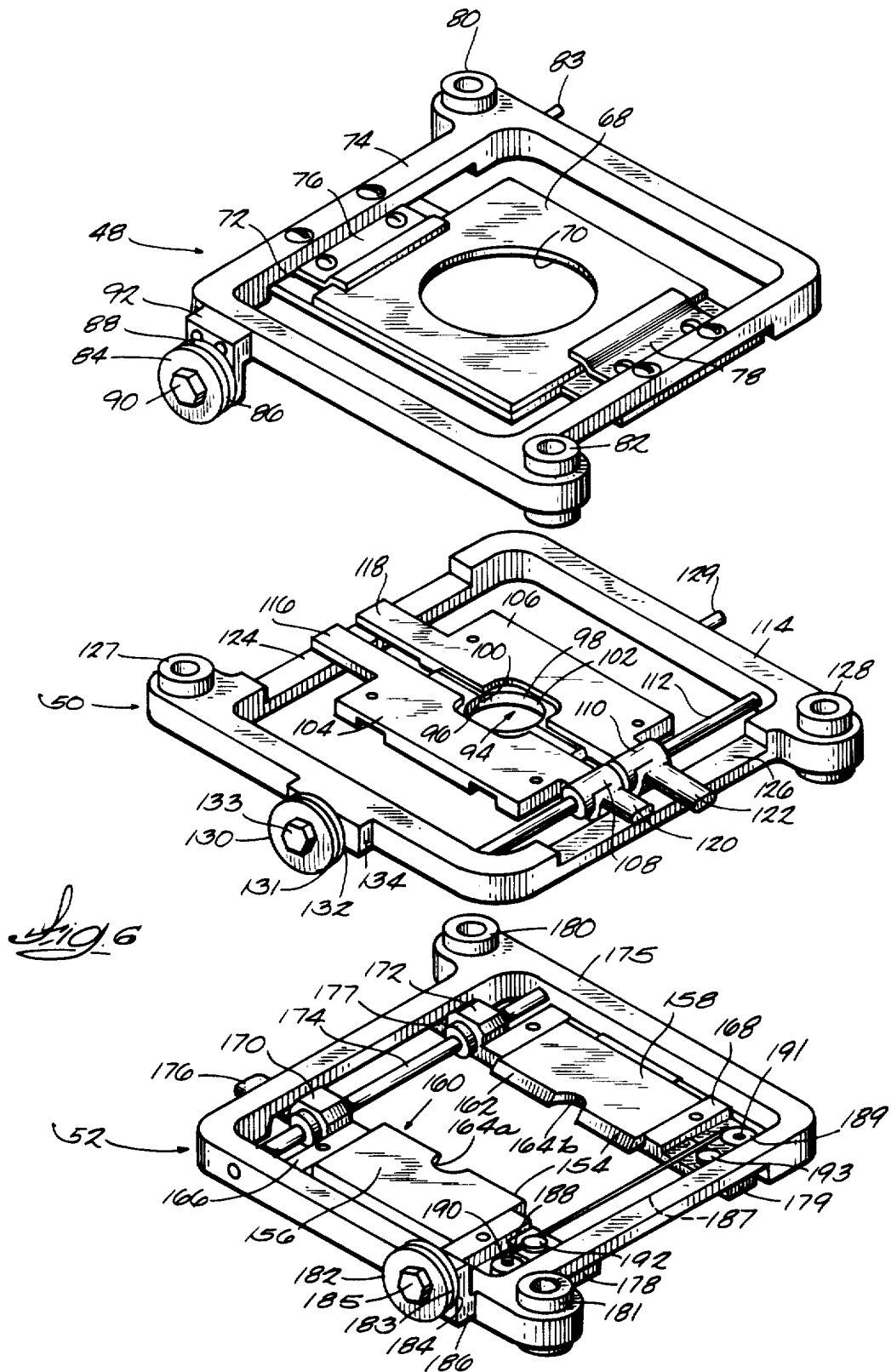

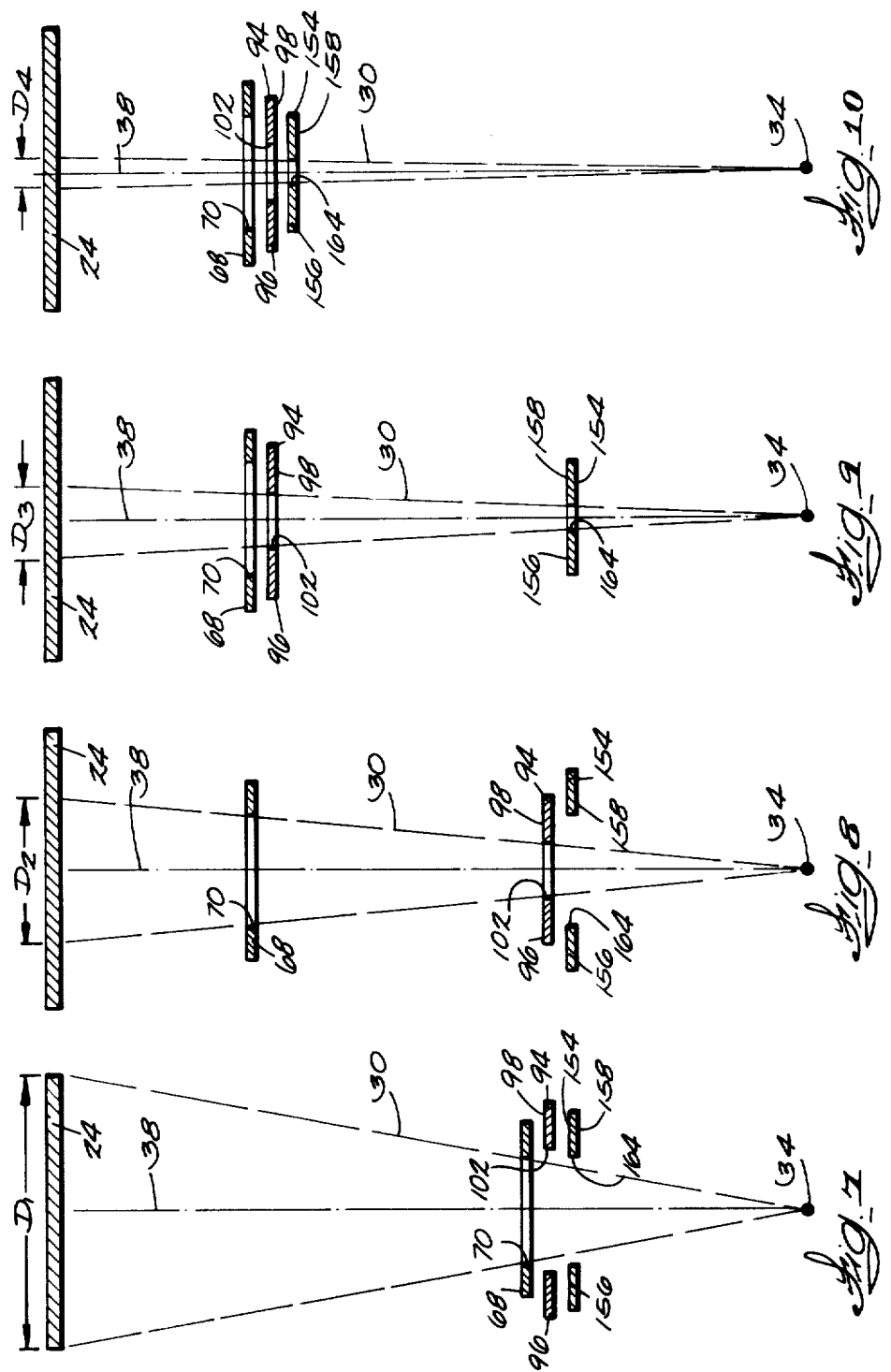

COLLIMATOR WITH ADJUSTABLE APERTURE

TECHNICAL FIELD

The present invention is a collimator for defining the size and shape of a pattern of radiation projected on a target. Such collimators are used, for example, for defining the boundaries of a beam of radiation emitted and detected in a medical diagnostic x-ray machine.

BACKGROUND OF THE INVENTION

Medical diagnostic x-ray machines typically comprise a source of x-rays, a flouroscopic, electronic, or photographic x-ray detector, and means for supporting a patient's anatomy of interest between the source and detector. A collimator must be interposed between the source and detector, and usually is positioned between the source and the patient, to confine the radiation to a beam of precise size and shape. The collimator limits the exposure of the patient to x-rays as much as possible, consistent with the aim of disclosing the patient's anatomy of interest.

Several types of collimators are known in the art. In plate collimators, one or more apertured plates disposed transversely to the direction of propagation of radiation are interposed in the beam of radiation. The radiation striking the plate beyond the margin of the aperture is deflected or absorbed. The beam projected through the aperture has a cross-sectional shape similar to that of the aperture and a size or diameter controlled by the position of the focal point of the radiation, the position and size of the aperture, and the position of the detector.

In some plate collimators, the size of the beam has been regulated by an iris diaphragm or similar structure. An iris diaphragm is cumbersome, since its leaves must be made of lead and thus are thick and heavy. An iris diaphragm also is not capable of producing a truly circular aperture, particularly for very small openings, and has a limited range of diameters. An iris is difficult to design if an unusual cross-sectional configuration for the x-ray beam is desired, such as a keyhole shape or the shape of an organ to be studied.

In other known plate collimators a plate (or series of plates) having apertures of various sizes has been interposed in the beam. These collimators are undesirable because the diameter of the pattern projected on the detector cannot be continuously adjusted.

SUMMARY OF THE INVENTION

The objects of the present invention are first, to provide a collimator for projecting on a detector a pattern of any size within a wide range; second to provide a collimator for projecting irregularly shaped patterns of any size; and finally, to provide both of the foregoing advantages in a collimator in which the moving elements have a short range of longitudinal travel.

The collimator of the present invention comprises at least one apertured collimating plate made of radiopaque material for providing continuous collimation. The collimating plate is positioned between the source of radiation and the detector so the beam of radiation must pass through its aperture. The plate can be moved from a first extremity of travel nearest the radiation source to a second extremity of travel in the direction of propagation of the beam of radiation, and can be stopped at any point along its travel. The distance of the plate from the focal point of the radiation source and the diameter of its aperture limit the solid angle described by the beam projected through the aperture, and thus the diameter of the pattern projected on the detector.

The collimator preferably includes a second collimating plate, having a second aperture smaller than the aperture of the first plate, positioned between the radiation source and the first plate. The second plate is provided with means to withdraw its radiopaque portions to an inactive position outside of the beam when the first plate is controlling the dimensions of the beam. Means are also provided to place the radiopaque portion of the second plate in an active position for regulating the beam dimensions. The second plate can be moved between a first extremity of travel nearest the radiation source and a second extremity of travel adjacent the first plate at its second extremity of travel. The diameter of the second aperture, the diameter of the first aperture, and their relative positions with respect to the source of radiation are such that when said second plate is in its active position at its first extremity of travel the beam projected through the second aperture is substantially identical in size, shape, and position to the beam projected through the first aperture at its second extremity of travel. As a result, after the first plate has been moved to its second extremity of travel the beam can be further collimated by advancing the second plate toward its second extremity of travel.

A third apertured plate can be provided between the focal point and second plate, including means to withdraw its radiopaque portions to an inactive position outside of the beam while either of the first two apertures is controlling the dimensions of the beam, and otherwise to advance its radiopaque portions to an active position for regulating the beam dimensions. The third aperture is smaller than the second aperture, and the third plate can be advanced from a first extremity of travel to a second one to further reduce the size of the beam. When both the second and third apertures are in their active positions the beam projected through the second aperture at its second extremity of travel is substantially identical to the beam projected through the third aperture at its first extremity of travel, resulting in still further reduction of the beam when the third plate is advanced.

In the preferred embodiment of the invention drive means are provided to advance each plate in turn from its first extremity of travel to its second extremity of travel while the other plates are held still. The drive is reversible so each plate can also be retracted in turn to its first extremity of travel. The successive travel of plates is preferably effected by an integrated mechanism.

In another preferred aspect of the invention, the means for moving a plate in and out of its active position is integrated with the means for advancing the preceding plate in the direction of propagation of the beam, so that as one plate reaches its second extremity of travel the aperture of the succeeding plate is in its active position before it begins to move from its first extremity to its second extremity of travel.

The apertures can be any shape. A pattern of any shape and size can thus be projected through the anatomy of interest, and then to the detector. In collimators having plural collimator plates, the plates require only a small longitudinal range of travel, since each plate travels in roughly the same region to reduce the size of the beam in successive stages. Even so, the diameter of the pattern projected on the detector can be varied over a wide range, and the range of variation can readily be increased by providing additional collimator plates in the assembly.

BRIEF DESCRIPTION OF DRAWINGS

FIG. 3 is a side elevation of the structure shown in FIG. 2.

FIG. 4 is a fragmentary rear elevation of the structure shown in FIG. 2.

FIG. 6 is an exploded perspective view of the collimator plates of FIG. 2, shown in isolation.

FIGS. 7, 8, 9, and 10 are simplified schematic cross-sectional views of the collimator of FIGS. 1-6 taken in the plane of its central ray, showing how its plates are successively advanced to reduce the dimentions of a beam in three stages.

DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structure. The details may be changed without departing from the invention, which is defined by the claims.

Figure 1:
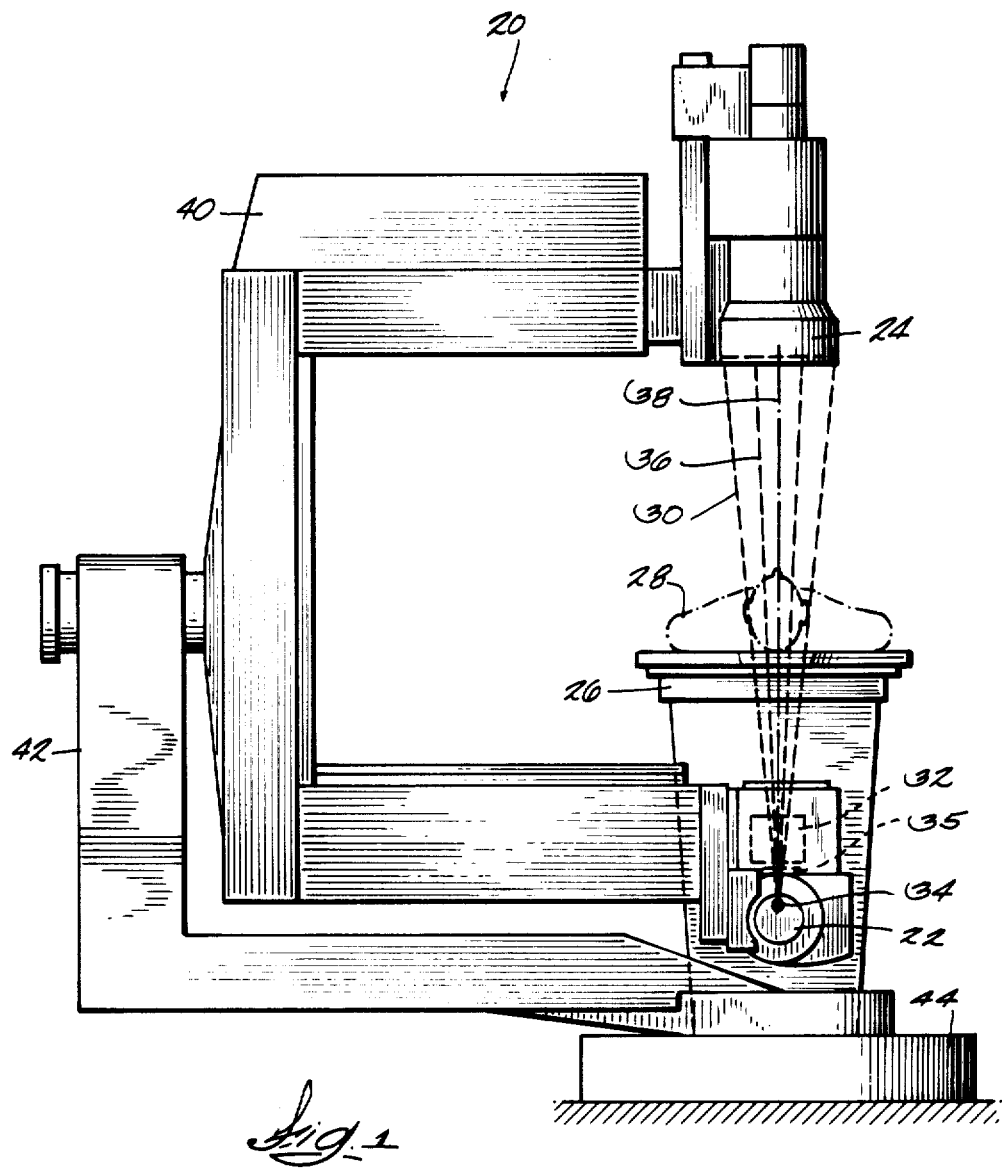
FIG. 1 is a schematic front elevation of a medical diagnostic x-ray machine, showing how the present invention can be positioned in such a machine.

FIG. 1 shows a typical medical diagnostic x-ray machine in which the collimator of the present invention is useful. The basic parts of machine 20 are a source 22 of x-rays or other suitable radiation, a detector 24 for such radiation (here an image intensifier), and a patient table 26 or other suitable means to support a patient 28 in the path of a beam 30 of x-rays. A collimator 32 is positioned between detector 24 and the focal spot 34 from which the x-rays are emitted, and usually between focal spot 34 and patient 28, to allow the dimensions of the x-ray beam projected on detector 24 to be continuously adjusted. A brass collar 35 not forming a part of the present invention supports a lead plate (not shown) interposed between focal spot 34 and collimator 32 to limit the size of beam 30 to the largest useful size for the machine. Beam 30 and beam 36 in FIG. 1 represent the maximum and minimum sizes for beams projected through collimator 32. (Hereinafter the beam is identified as 30 without regard to its size.) Central ray 38 represents the direction of propagation of beam 30 and the longitudinal axis between source 22 and detector 24. Although FIG. 1 shows only one detector for the radiation passing through patient 28, in typical systems several detectors, which can be photographic, fluoroscopic, or electronic, are provided in a single machine. Also, both source 22 and detector 24 are translatable along central ray 38, so the distance between source 22 and detector 24 is not fixed.

Source 22 and detector 24 are supported by a structure known as an L/U arm, comprising a U-shaped member 40 supporting source 22 and detector 24, pivotally attached to and supported by an L-shaped member 42. Member 42 is pivotally attached to a base member 44. This construction allows U-shaped member 40 to be revolved about a horizontal axis perpendicular to central ray 38 and about a vertical axis collinear with central ray 38, allowing the beam of radiation to be passed through the patient in a wide variety of directions.

FIGS. 2-6 show the parts of collimator 32 in more detail. Collimator 32 comprises a first collimating plate assembly 48, a second collimating plate assembly 50, and a third collimating plate assembly 52. The plate assemblies are slidably carried by a frame 54 comprising first and second frame members 56 and 58 joined by guide rods 60, 62, 64, and 66 and fixed with respect to focal spot 34.

Turning now to FIG. 6, first plate assembly 48 comprises a plate 68 which is substantially radiopaque to the radiation of choice. First plate 68 has an aperture 70 which here is circular in transverse cross-section. A circular shape is chosen here to provide a pattern of radiation corresponding to the circular shape of detector 24. However, in the present collimator aperture 70 can be any shape, such as the cross-sectional shape of a particular organ to be studied.

A backing member 72 is bolted to a frame 74, and brackets 76 and 78 attached to backing member 72 hold plate 68 in place against backing member 72. Plate assembly 48 is equipped with linear bearing sleeves 80 and 82 attached to diagonally opposed ears extending from frame 74. Bearing sleeve 82 receives guide rod 62 and bearing sleeve 80 receives guide rod 64 (see FIG. 5) to maintain first plate 68 perpendicular to central ray 38 while allowing plate assembly 48 to be driven along the guide rods between its first and second extremities of travel. A peg 83 is provided for latching first plate assembly 48 at its second extremity of travel, as explained below. Assembly 48 also includes a pulley 84 having first and second sheaves 86 and 88 independently pivotally mounted on a bearing shaft defined by stud 90, which in turn is attached to a bracket 92 fixed to the front of frame 74. Pulley 84 is part of the drive mechanism described below for moving first plate assembly 48 between its first and second extremities of travel.

Second plate assembly 50 comprises a second plate 94 made of radiopaque material and split into two segments, 96 and 98. These segments can be closed together at parting surface 100 (as in FIG. 6) to define a second aperture 102 which is smaller than first aperture 70. When segments 96 and 98 are closed together second plate assembly 50 is in its active position intersecting the beam; when segments 96 and 98 are moved apart, plate assembly 50 is in its inactive position and does not intersect the beam.

Segments 96 and 98 are respectively mounted to backing members 104 and 106 for support. Backing members 104 and 106 have linear bearings 108 and 110 for being slidably supported by a guide rod 112 fixed to frame 114. Ears 116, 118, 120, and 122 rest on bearing surfaces 124 and 126 to prevent rotation of backing members 104 and 106 about guide rod 112. Second aperture 102 can be opened by spreading backing members 104 and 106 apart so segments 96 and 98 do not intersect the beam projected through first aperture 70 for any position of first plate assembly 48. Second aperture 102 can be closed by pushing backing members 104 and 106 together. A mechanism for doing this is described below.

Second plate assembly 50 further includes linear bearing sleeves 127 and 128 for receiving guide rods 60 and 66 to permit second plate assembly 50 to slide up or down between assemblies 48 and 52 while remaining perpendicular to central ray 38. Bearings 127 and 128 are staggered with respect to bearings 80 and 82 so that the first and second plate assemblies can be nested closely together when they are adjacent. A peg 129 is provided for latching second plate assembly 50 at its second extremity of travel, as explained below. Finally, second plate assembly 50 includes a pulley 130 having first and second sheaves 131 and 132 independently pivotally mounted to frame 114 by a stud 133 fixed to bracket 134.

Third plate assembly 52 is constructed substantially the same as second plate assembly 50, but the parts are rearranged somewhat to provide closer nesting between the second and third plate assemblies 50 and 52 when they are adjacent each other. Third plate assembly 52 comprises a third plate 154 made of radiopaque material and divided into two segments, 156 and 158, having inwardly opposed surfaces 160 and 162 which interface when the segments are brought together onto an active position to form a third aperture 164 defined by wall portions 164a and 164b. Third aperture 164 is smaller than second aperture 102 (when plate assemblies 50 and 52 are each in their active position.) Segments 156 and 158 are respectively carried on backing members 166 and 168 having linear bearing sleeves 170 and 172 slidably carried on a guide rod 174 fixed to frame 175 for allowing third aperture 164 to be opened by spreading apart backing members 166 and 168 so segments 156 and 158 do not intersect the beam projected through apertures 70 or 102 for any position of first plate assembly 48 or for any position or state of second plate assembly 50. Projecting ears 176, 177, 178, and 179 of backing members 166 and 168 prevent rotation of the backing members about guide rod 174. As before, the ears slide along bearing surfaces (not shown) and are provided with a lever arrangement (described below) to open or close aperture 164.

As before, frame 175 supports linear bearing sleeves 180 and 181 for receiving guide rods 64 and 62, allowing third plate assembly 52 to be held perpendicular to central ray 38 while being translated between its first extremity of travel adjacent first frame member 56 and its second extremity of travel. Bearings 180 and 181 are staggered with respect to bearings 140 and 142 and are aligned with bearings 80 and 82, allowing the plates to be nested closely when they are adjacent.

Finally, third plate assembly 52 is provided with a pulley 182 having first and second sheaves 183 and 184 independently pivotally carried on a stud 185 fixed to bracket 186, which in turn is fixed to frame 175, for allowing third plate assembly 52 to be driven to or supported at any position along guide rods 64 and 62.

In this embodiment of the invention first plate 68 is made of lead and is 0.125 inches (3.18 millimeters) thick. Aperture 70 has a diameter of 1.76 inches (44.7 millimeters). Second plate 94, when closed so that its facing surfaces mate, has a parting line inclined 45 degrees with respect to the plane of the plate (to prevent radiation leakage when second aperture 102 is closed to its working diameter). Second plate 94 is made of lead and is 0.125 inches (3.18 millimeters) thick. When closed, second aperture 102 is circular and has a diameter of 0.82 inches (20.8 millimeters). Third plate 154 is made of lead of the same thickness as the other plates, also has its parting surface inclined 45 degrees, and has a third aperture 164, when closed, of diameter 0.38 inches (9.7 millimeters).

Although other materials can be used, in this embodiment frames 74, 114, and 175 are made of aluminum, as are backing plates 72, 104, 106, 166, and 168. Frame members 56 and 58 are made of steel. The sheaves of the pulleys are each made of aluminum, and most of the other hardware is made of steel.

The mechanisms shown in FIGS. 2-6 for opening and closing apertures 102 and 164 can now be described. The mechanisms for each aperture are essentially identical; some parts of each mechanism are not visible in the figures.

Figure 5:
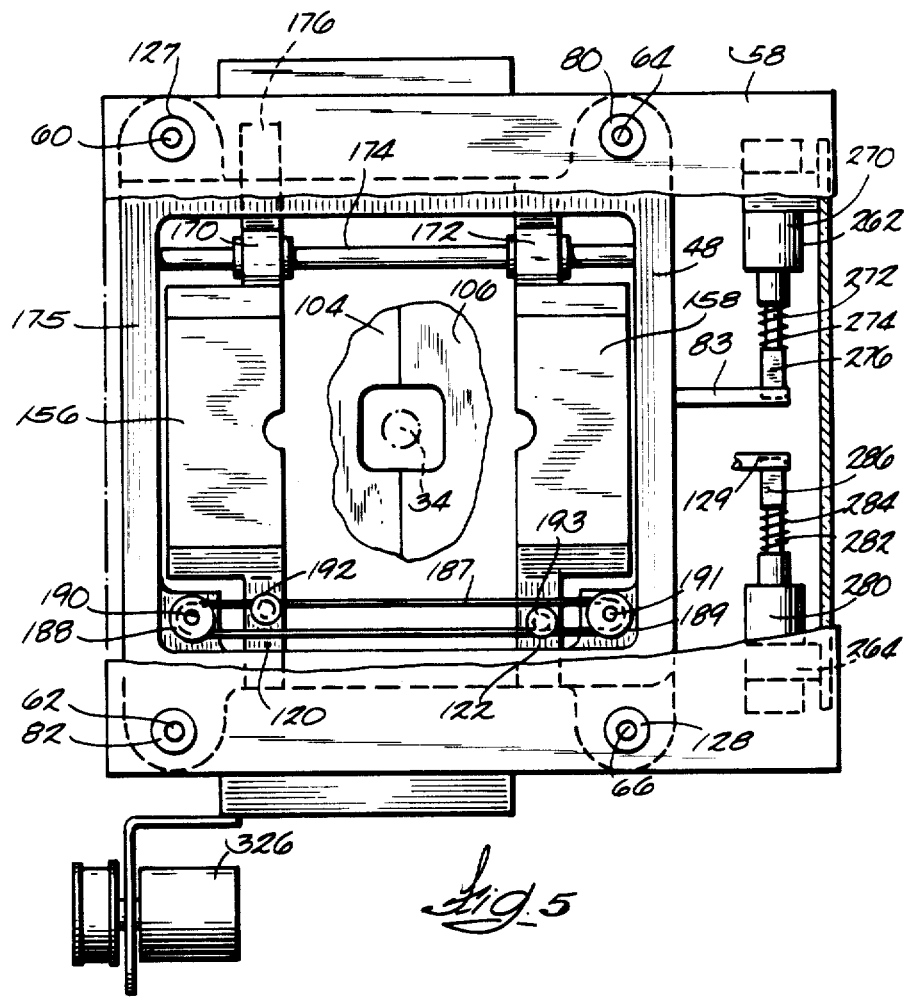
FIG. 5 is a plan view of the structure shown in FIG. 2, partially cut away and having its upper plate assembly removed to show detail.

FIGS. 5 and 6 show the mechanism for closing or opening aperture 164 by moving backing members 166 and 168 equally and oppositely when ear 176 is manipulated as described below. Cable loop 187 is supported by pulleys 188, 189 attached by pivots 190, 191 to frame 175. Studs 192, 193 respectively secure first and second runs of loop 187 to backing members 166 and 168. As a result, movement of either backing member is transmitted by loop 187 to the other backing member. A similar structure, not visible in the figures, is provided to open and close aperture 102, when ear 122 is manipulated.

Figure 2:
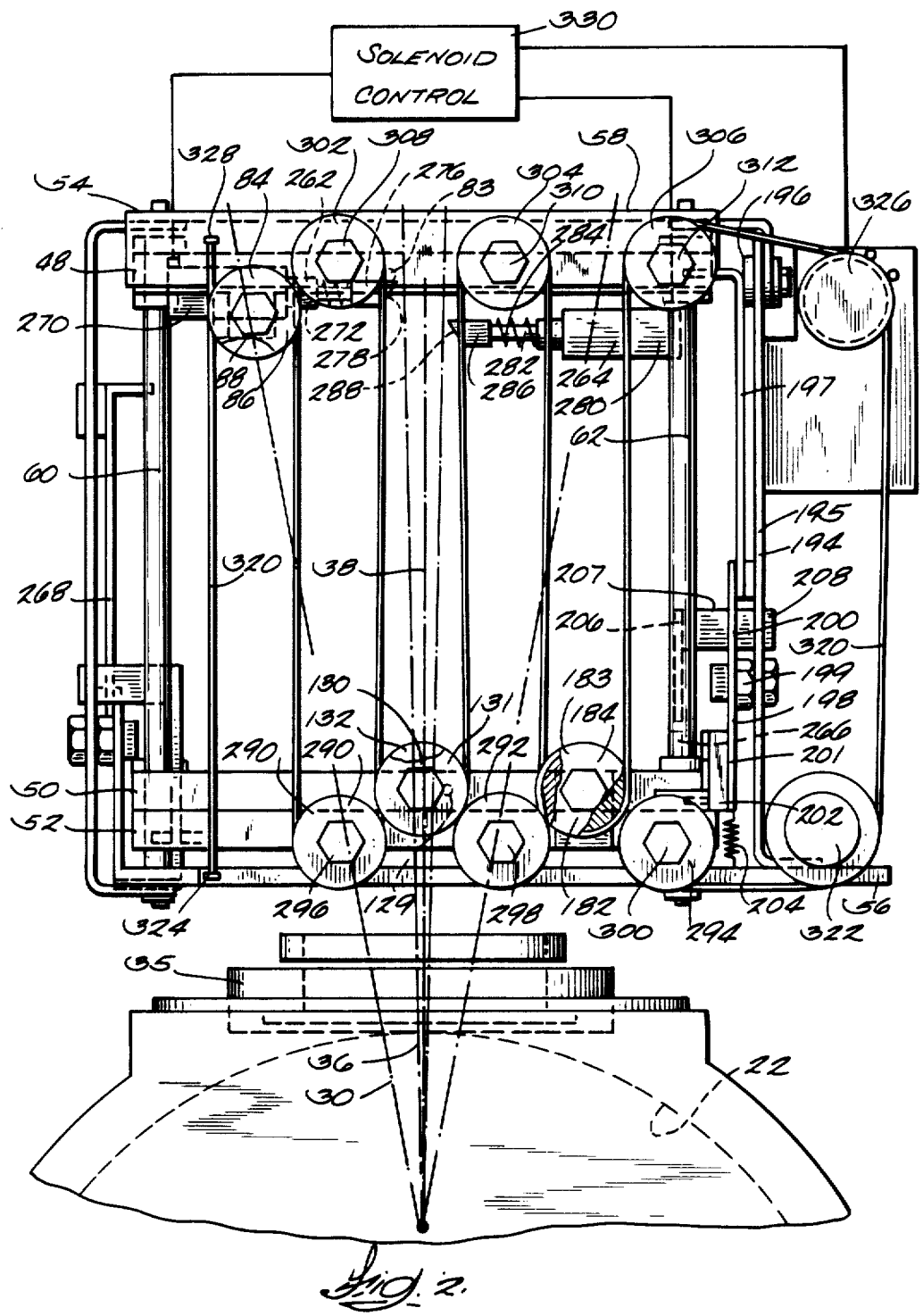
FIG. 2 is a front elevation of the present invention, greatly enlarged compared to FIG. 1, showing it in relation to a radiation source.

FIGS. 2, 3, and 4 show how ear 122 is manipulated to open and close aperture 102; the aperture has just been closed or is just about to be opened in these figures, depending on whether the x-ray beam diameter is being decreased or increased. Ear 122 is engaged by a linkage supported by a plate 194 secured to frame 54; the linkage responds to movement of first plate assembly 48 to close aperture 102 as assembly 48 approaches its second extremity of travel and to open aperture 102 and secure assembly 50 at its first extremity of travel shortly after assembly 48 leaves its second extremity of travel. The linkage comprises a slot 195 in plate 194; a slide 196 constrained to sliding travel in slot 195; an L-shaped link 197 pivotally attached at its upper end to slide 196 and having a horizontally extending finger portion for being lifted by frame 74; a bell crank 198 secured by a pivot 199 to plate 194 and having a first arm 200 pivotally attached to the lower end of link 197 and a second arm 201 having pushing members 202, 203 for sliding ear 122 back and forth; and a spring 204 to bias bell crank 198 for counterclockwise rotation. When frame 74 is at its second extremity of travel (as shown), aperture 102 is closed to its working diameter. Nothing prevents ear 122 from being lifted from between members 202 and 203, as it is clear of plate 205.

If frame 74 is moved downward link 197 follows, allowing bell crank 198 to rotate counterclockwise due to its bias. Pushing member 202 pushes ear 122 to the right underneath plate 205, which is attached to plate 194 by plates 206, 207, and 208. The interference between ear 122 and plate 205 when the aperture is open acts as a latch to prevent second plate assembly 50 from being lifted away from its first extremity of travel until first plate assembly 48 has reached its second extremity of travel. The downward travel of slide 196 is limited by slot 195, so when first plate assembly 48 is approaching its first extremity of travel it is clear of the lever mechanism for opening and closing the aperture of second plate assembly 50. The process is reversed to move ear 122 to the left (FIG. 3) for closing second aperture 102 and allowing second plate assembly 50 to be lifted clear of plate 205. A similar structure, not visible in detail in the figures, is provided to manipulate ear 176 responsive to the position of frame 114.

Latching assemblies 262 and 264 are fixed to frame member 58; they independently latch first and second plate assemblies 48 and 50 at their second (upper) extremities of travel. The latching assemblies cooperate with the drive mechanism disclosed below to allow the plates to be driven in sequence from their first extremities of travel.

Latch assembly 262 is shown engaging peg 83 of first plate assembly 48 for holding it at its upward extremity of travel (see FIG. 5). Latch assembly 262 comprises a solenoid 270, a soft iron plunger 272, a compression spring 274 to bias plunger 272, and a ramp latch 276 having a beveled forward face 278 (see FIG. 2). Latch assembly 264 for engaging peg 129 to hold second plate assembly 50 at its second extremity of travel similarly comprises a solenoid 280, plunger 282, compression spring 284, ramp latch 286, and beveled forward face 288.

Latch assemblies 262 and 264 work identically, so only the operation of latch assembly 264 will be described explicitly. When second plate assembly 50 is between its extremities of travel, peg 129 is clear of latch 286. When plate assembly 50 is raised to its second extremity of travel, peg 129 bears upward against forward face 288, retracting ramp latch 286 against the bias of spring 284. When peg 129 advances above ramp latch 286 the latch is shot, locking peg 129, and thus plate assembly 50, in place. When plate assembly 50 is to be lowered, the plunger is withdrawn into the solenoid by passing a pulse of electrical current through the solenoid circuit, allowing peg 129 to escape when second plate assembly 50 is lowered. The means for doing this is explained below.

FIG. 2 best shows the mechanism for driving each plate assembly up and down. Pulleys 290, 292, and 294 are single sheave pulleys rotatably fixed to first frame member 56 by studs 296, 298 and 300. Similarly, pulleys 302, 304, and 306 are single sheave pulleys rotatably carried on studs 308, 310, and 312, each fixed to a downturned edge of second frame member 58.

A single cable 320 interconnects drum drive 322 and the several pulleys and cooperates with latch assemblies 262 and 264, and with the previously described linkages generally indicated at 266 and 268 for latching the second and third plate assemblies 50 and 52 at their first extremities of travel, to drive the individual plates successively from their first extremities to their second extremities of travel. Cable 320 has a first end 324 attached to frame member 56. Starting at first end 324, the cable is reeved over first sheave 86 of pulley 84; under pulley 290; over first sheave 131 of pulley 130; under pulley 292; over first sheave 183 of pulley 182; under pulley 294; around drum drive 322; around cable drive potentiometer 326; over pulley 306; under second sheave 184 of pulley 182; over pulley 304; under second sheave 132 of pulley 130; over pulley 302; and under second sheave 88 of pulley 84. Cable 320 terminates at a second end 328 fixed to frame member 58. For purposes of illustrating and claiming the invention, the run reeved over pulley 84 is a first run, the run reeved under pulley 84 is a second run, the run reeved around drive 322 is a third run, the run reeved over pulley 130 is a fourth run, the run reeved under pulley 130 is a fifth run, the run reeved over pulley 182 is a sixth run, and the run reeved under pulley 182 is a seventh run of cable.

To see how the drive works, first consider the situation in FIG. 2, in which plate assemblies 48 and 52 are latched, respectively in their second and first extremities of travel, and second plate assembly 50 is unlatched in preparation for being advanced from its first to its second extremity of travel. In this situation, pulley 130 is the only one that is free to move vertically. When drum drive 322 is motionless the fifth run of cable reeved under second sheave 132 of pulley 130 prevents pulley 130 from moving downward, and the fourth run of cable reeved over the first sheave 131 of pulley 130 prevents plate assembly 50 from moving upward, so second plate assembly 50 is prevented from being raised or lowered. To raise second plate assembly 50 compared to its position in FIG. 2, drum drive 322 is driven clockwise, thus slackening the fourth run of cable and at the same time drawing in and thus shortening the fifth run of cable. Pulley 130, and thus second plate assembly 50, moves toward its second extremity of travel as a result. Since the rate of slackening of one run is the same as the rate of drawing in of the other run, and since the two sheaves travel the same distance in the same direction, no noticeable slack is created, the only movement visible on casual observation being that of the second plate assembly. To lower the second plate assembly, drum drive 322 is driven counterclockwise, thus slackening the fifth run of cable and drawing in the fourth run of cable.

This basic principle of operation will be seen to apply equally to drive pulley 130, pulley 84, or pulley 182 when the plate assemblies attached to the other two pulleys are latched. Pulley 182 is driven by slackening one of the sixth and seventh runs and drawing in the other run; pulley 84 is driven by slackening one of the first and second runs and drawing in the other one. The control mechanism which makes the successive movement of plates possible operates by latching the two plates which are not in motion and allowing the remaining plate to travel one way or the other, responsive to rotation of drum drive 322. The pulleys attached to latched plates merely guide the cable and are immobile while the remaining pulley is being moved.

The solenoid control means shown schematically in FIG. 2 works as follows. The resistance of potentiometer 326 changes as cable 320 is driven, and is a measure of the positions of plate assemblies 48, 50, and 52. A signal passed via potentiometer 326 to solenoid control 330 thus experiences a voltage drop related to the positions of the plate assemblies. When the value of this voltage drop corresponds to a condition in which a plate assembly is about to depart from its second extremity of travel the corresponding solenoid is energized to momentarily release the latch which otherwise secures the plate assembly, then deenergized after the plate assembly has moved sufficiently to escape the latch.

Now that the details have been described the principle of operation of the collimator can be explained with reference to FIGS. 7–10. FIG. 7 shows plates 68, 94, and 154 at their first extremities of travel. At this point first aperture 70 defines the maximum possible diameter, denoted here as $D_1$, of the pattern striking detector 24. Segments 96 and 98 of second plate 94 are separated, as are segments 156 and 158 of third plate 154.

FIG. 8 shows the situation after first plate 68 has been moved to its second extremity of travel. Second plate 94 remains at its first extremity of travel, and segments 96 and 98 of second plate 94 are drawn together to close second aperture 102. At this point first aperture 70 and second aperture 102 define identical patterns of radiation, each having a diameter $D_2$. Segments 156 and 158 of third plate 154 are still spread apart in FIG. 8, so they do not affect the beam.

Looking now at the situation in FIG. 9, first plate 68 and second plate 94 are at their second extremities of travel. Third plate 154 remains at its first extremity of travel, and its aperture has just been closed. First aperture 70 is now too large to have any effect on the diameter of the beam, while apertures 102 and 154 define identical patterns each having a diameter $D_3$.

FIG. 10 shows the situation when all three plates are at their second extremities of travel. The first and second apertures 70 and 102 are now too large to have any effect on the diameter of the beam, so third aperture 164 solely determines the minimum diameter $D_4$ of the pattern projected on the detector. Since third plate 154 is held in place by the cable drive in the preferred embodiment, there is no need to provide a latch to latch it at its second extremity of travel. Rather, it is held by the cable until the beam diameter is to be increased. The drive is then reversed to retract third plate 154 to its first extremity of travel, at which time the solenoid of latch 264 is energized, allowing retraction of second plate 94 to its first extremity of travel (meanwhile spreading segments 156 and 158 a-part). Finally, the solenoid of latch assembly 262 is energized, allowing retraction of first plate 68 to its first extremity of travel (meanwhile spreading segments 96 and 98 apart).

The collimator just described is capable of continuously collimating a beam of radiation in three stages. The advantage of collimating in three stages instead of in one stage is evident from FIGS. 7 to 10. Three plates traveling about the same distance through about the same region provide a much greater variation in field size (D) than any single plate traveling the same distance through the same region could provide.

Figures 11, 12, 13:
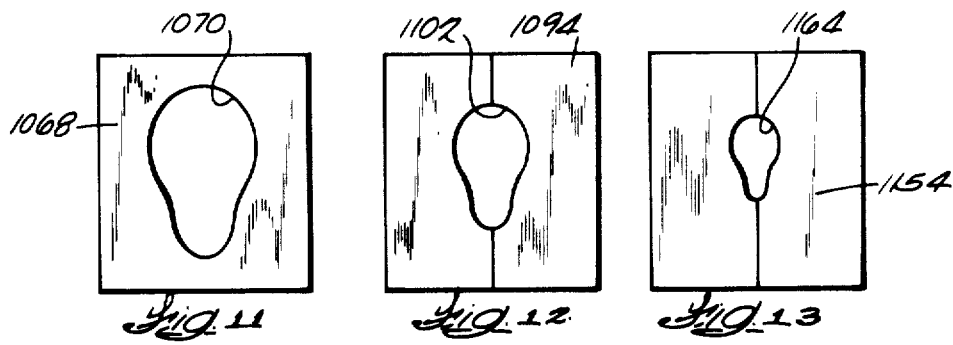
FIGS. 11, 12, and 13 are schematic plan views of collimator plates employed in a second embodiment of the invention in which a pattern of radiation having an irregular shape can be projected onto the radiation detector.

FIGS. 11, 12, and 13 show first, second, and third collimator plates 1068, 1094, and 1154 for use in an alternate embodiment of the invention in which a beam having a keyhole-shaped cross-section is projected through the collimator. Such a pattern corresponds to the shape of a patient's head and neck, and can be used when only those areas of the anatomy are to be exposed to radiation. Apertures 1070, 1102 and 1164 have similar shapes but are different sizes, just like apertures 70, 102, and 164; plates 1094 and 1154 are also split through their apertures to allow the corresponding plates to be spread apart into their inactive positions, just like plates 94 and 154. Thus, if the plates of FIGS. 11, 12, and 13 are used in place of plates 68, 102, and 164, providing their apertures are properly proportioned, a keyhole-shaped beam will be projected, the cross-sectional size of which can be continuously varied without affecting its cross-sectional shape.

The same principle can be applied to produce collimators for projecting beams of any conceivable cross-sectional shape and variable size for selectively exposing any organ to radiation. For example, a kidney-shaped beam can be used for kidney studies, a liver-shaped beam can be used for liver studies, and so forth. The same plates can be used for patients having organs of different sizes, and there is no need to restrict the permissible positions or separation of source and detector because the collimator can correct the size of the beam to accommodate the desired positions of the source and detector.

We claim:

1. A collimator for being positioned between a source of x-radiation and a detector to regulate the size of the pattern of radiation projected onto said detector, comprising:

a first collimating plate located on a longitudinal axis between said radiation source and said detector, said plate being made of radiopaque material and having a first circular aperture to pass a portion of radiation from said source for said aperture to define a radiation pattern presented to said detector;

first drive means for advancing said first plate along said axis from a first extremity of travel nearest said radiation source to a second extremity of travel further from said radiation source for said aperture to reduce the angle of divergence and the diameter of said beam projected on said detector;

a second collimating plate made of radiopaque material and having a second circular aperture smaller than said first aperture;

means for selectively placing said second collimating plate in an active position between said radiation source and said first collimating plate such that said second aperture defines the size of said radiation pattern;

means for selectively removing said second collimating plate from said active position to an inactive position such that it no longer defines the size of said radiation pattern; and second drive means for advancing said second plate along said longitudinal axis from a first extremity of travel nearest said radiation source to a second extremity of travel further from said radiation source when said second plate is in said active position to further reduce the size of said pattern.

2. The collimator according to claim 1, wherein said first and second drive means are integrated and comprise:

first and second stationary frame members, respectively located closer to and further from said source of radiation than said plates;

first and second double sheave pulleys respectively pivotally attached to said first and second plates;

a reversible drum drive;

a cable having first and second ends respectively fixed to said first and second frame members, first and second runs reeved from said respective ends around the respective sheaves of said first pulley, a third run between said first and second runs reeved around said drum drive, and fourth and fifth runs respectively between said first run and third run and between said second run and third run, said fourth and fifth runs reeved around the respective sheaves of said second pulley; and latch means to hold one of said plates stationary at either extremity of its travel when the other plate is to be moved;

whereby, when either plate is latched, the other is advanced toward said second frame member by rotating said drum drive one way and retracted toward said first frame member by reversing said drum drive.

3. The collimator of claim 1, wherein the pattern of radiation projected through said first aperture when said first collimating plate is at its second extremity of travel is substantially congruent to the pattern of radiation projected through said second aperture when said collimating plate is at its first extremity of travel and said second aperture is in said active position.

4. The collimator of claim 1, further comprising:

a third collimating plate made of radiopaque material and having a third aperture smaller than said second aperture;

means for selectively placing said third collimating plate in an active position such that said third aperture defines the size of said radiation pattern;

means for selectively removing said third collimating plate from said active position to an inactive position such that it no longer defines the size of said radiation pattern; and third drive means for advancing said third plate along said longitudinal axis from a first extremity of travel nearest said source of radiation to a second extremity of travel further from said source of radiation when said third plate is in said active position to still further reduce the size of said pattern.

5. The collimator according to claim 1 or 4, wherein said second plate is split through its aperture into plural segments, and wherein said means for selectively placing or removing said second plate into or from its active position comprises a first mechanical linkage for spreading said second plate segments apart or drawing them together to increase or decrease the size of said second aperture.

6. The collimator of claim 5, wherein said first linkage cooperates with said first plate to draw said second plate segments together when said first plate approaches its second extremity of travel and to spread said second plate segments apart when said first plate leaves its second extremity of travel.

7. The collimator of claim 4, wherein said first, second, and third drive means are integrated and comprise:

first and second stationary frame members respectively located closer to and further from said source of radiation than said plates;

first, second, and third double sheave pulleys respectively pivotally attached to said first, second, and third plates;

a reversible drum drive;

a cable having first and second ends respectively fixed to said first and second frame members, first and second runs reeved from said respective ends around the respective sheaves of said first pulley, a third run between said first and second runs reeved around said drum drive, fourth and fifth runs respectively between said first run and third run and between said second run and third run, said fourth and fifth runs reeved around the respective sheaves of said second pulley, and sixth and seventh runs respectively between said third run and fourth run and between said third run and fifth run, said sixth and seventh runs reeved around the respective sheaves of said third pulley; and latch means to hold all but one of said plates stationary, each at one extremity of its travel, when the remaining plate is to be moved.

8. The collimator of claim 4, wherein said third plate is split through its aperture into plural segments, and wherein said means for selectively placing or removing said third plate into or from its active position comprises a second mechanical linkage for spreading said segments apart or drawing them together to increase or decrease the size of said third aperture.

9. The collimator of claim 8, wherein said second linkage cooperates with said second plate to draw said third plate segments together when said second plate approaches its second extremity of travel and to spread said third plate segments apart when said second plate leaves its second extremity of travel.

* * * * *